(12) United States Patent
Weis

(10) Patent No.: US 12,268,365 B2
(45) Date of Patent: Apr. 8, 2025

(54) ENDOSCOPE REPROCESSING DEVICE AND FLOW CONTROL UNIT THEREFORE, METHOD OF OPERATING A FLOW CONTROL UNIT AND AN ENDOSCOPE REPROCESSING DEVICE

(71) Applicant: OLYMPUS Winter & Ibe GmbH, Hamburg (DE)

(72) Inventor: Antonia Weis, Hamburg (DE)

(73) Assignee: Olympus Winter & Ibe Gmbh, Hamburg (DE)

( * ) Notice: Subject to any disclaimer, the term of this patent is extended or adjusted under 35 U.S.C. 154(b) by 0 days.

(21) Appl. No.: 18/370,038

(22) Filed: Sep. 19, 2023

(65) Prior Publication Data

US 2024/0215811 A1    Jul. 4, 2024

Related U.S. Application Data

(60) Provisional application No. 63/436,918, filed on Jan. 4, 2023.

(51) Int. Cl.
*A61B 1/12* (2006.01)
*A61B 1/015* (2006.01)

(52) U.S. Cl.
CPC .............. *A61B 1/123* (2013.01); *A61B 1/015* (2013.01)

(58) Field of Classification Search
None
See application file for complete search history.

(56) References Cited

U.S. PATENT DOCUMENTS

2019/0076009 A1    3/2019   Yang

*Primary Examiner* — Rita P Adhlakha
(74) *Attorney, Agent, or Firm* — Scully, Scott, Murphy & Presser, P.C.

(57) ABSTRACT

A flow control unit for use with an endoscope reprocessing device, the flow control unit including: a main fluid supply line coupled to an inlet, the inlet receives processing fluid from a fluid source, at least one supply channel supplying the processing fluid to an internal channel of an endoscope, the at least one supply channel is coupled to the main fluid supply line, a dedicated switchable valve in the supply channel for opening the supply channel to pass the processing fluid through the supply channel or closing the supply channel to block the flow, and a processor for operating the switchable valve according to a reprocessing routine, and upon termination of the reprocessing routine, set the switchable valve to a safe switching state in which a flow rate through the main supply line is lower than a maximum flow rate through the main supply line.

19 Claims, 2 Drawing Sheets

ENDOSCOPE REPROCESSING DEVICE AND FLOW CONTROL UNIT THEREFORE, METHOD OF OPERATING A FLOW CONTROL UNIT AND AN ENDOSCOPE REPROCESSING DEVICE

CROSS-REFERENCE TO RELATED APPLICATION

The present application is based upon and claims the benefit of priority from U.S. Provisional Patent Application No. 63/436,918, filed on Jan. 4, 2023, the entire contents of which is incorporated herein by reference.

BACKGROUND

Field

The present disclosure relates to a flow control unit for an endoscope reprocessing device and to an endoscope reprocessing device comprising such a flow control unit. Furthermore, the present disclosure relates to a method of operating a flow control unit for an endoscope reprocessing device and to a method of operating an endoscope reprocessing device.

Prior Art

Endoscope reprocessing devices, for example the ETD series of Olympus, generally have a washing cabinet for receiving surgical instruments such as endoscopes to be reprocessed. In the washing cabinets, there are for example baskets for receiving the endoscopes. Adapters are provided in the washing cabinet with which the endoscope channels can be connected to supply channels of the endoscope reprocessing device. During reprocessing, the reprocessing device circulates a reprocessing fluid through the various endoscope channels. The reprocessing fluid is for cleaning and disinfecting the inner endoscope channels after use. After completion of the cleaning and disinfection routine, reprocessing of the endoscope continuous with switching over to the drying routine. During drying, the endoscope channels are flushed with air. The drying air is often supplied by a pressurized air source. The pressurized air source can be for example a local compressor. However, in many cases, the reprocessing device is coupled to a centralized compressed air supply of the facility in which the reprocessing device is operated. For example, the reprocessing device is coupled to a central pressurized air supply of a medical facility such as a hospital.

The reprocessing device comprises a flow control unit, which is located at the interface between the reprocessing fluid and pressurized air supplies and the washing cabinet. A flow control unit is for example known from unpublished U.S. 63/428,493. The flow control unit receives the processing fluid, which can be the reprocessing fluid or the pressurized air from respective sources, and distributes it into one or more of supply channels. Every supply channel is equipped with a dedicated controllable valve, for example with an electronically controllable valve. The supply channels are dedicated channels in that every supply channel is for individually reprocessing one of the different endoscope channels. For performance of a reprocessing program, the flow control unit performs different reprocessing routines. For example, there is a washing routine, a subsequent disinfection routine and a final drying routine. The individual reprocessing routines can be performed in the named order. They can also be repeated, for example in the order washing/disinfection/washing/drying. All reprocessing routines together represent the reprocessing program.

During performance of a reprocessing program, the reprocessing device consumes a certain amount of reprocessing fluid and compressed air. Because the compressed air is often provided by a centralized compressed air system of a medical facility, the consumption of compressed air by the reprocessing device influences the central system. The total consumption of compressed air by the reprocessing device is distributed over time and therefore in most cases does not influence the stability of the centralized compressed air system. However, a maximum flow of compressed air that can be fed through the endoscope reprocessing device, which means the maximum consumption of compressed air of a reprocessing device, can be rather high. This can result in a critical situation, if a plurality of endoscope reprocessing devices are installed in a medical facility and, in addition to this, are operated simultaneously. Furthermore, endoscope reprocessing devices are often installed in a certain limited area of the medical facility, for example near to a surgical area. In a situation in which a plurality of endoscope reprocessing devices are simultaneously operated in the limited area, the total compressed air consumption of the reprocessing devices can be rather high. This temporary high consumption of compressed air can affect the centralized compressed air supply of the medical facility in an undesired way.

SUMMARY

It is an object to provide a flow control unit for an endoscope reprocessing device, an endoscope reprocessing device, a method of operating a flow control unit for an endoscope reprocessing device and a method of operation an endoscope reprocessing device which overcomes at least some of the aforementioned technical drawbacks.

Such object can be solved by a flow control unit for an endoscope reprocessing device, comprising:
- a main fluid supply line coupled to an inlet, wherein the inlet is configured to receive processing fluid from a fluid source,
- at least one supply channel for supplying the processing fluid to at least one internal channel of an endoscope, wherein the at least one supply channel is fluidically coupled to the main fluid supply line,
- at least one dedicated switchable valve intergrated in the supply channel, wherein the switchable valve is configured to open or close the supply channel in that a flow of the processing fluid passes through the supply channel or is blocked, and
- a processor comprising hardware, is the processor being configured to operate the at least one dedicated switchable valve according to a reprocessing routine, wherein the processor is further configured, upon termination of the reprocessing routine, to set the at least one dedicated switchable valve to a safe switching state, wherein in the safe switching state a flow rate through the main supply line is lower than a maximum flow rate through the main supply line.

The processor can be implemented as a physical part or physical entity of the flow control unit. The processor can also be implemented as software in a central processing unit (CPU) of the reprocessing device. Furthermore, there is a reprocessing program including at least one reprocessing routine. The reprocessing program and/or the least one reprocessing routine can be stored on a non-volatile storage medium. This storage medium can be a physical entity of the processor of the flow control unit. The reprocessing program or a reprocessing routine can also be provided to the flow control unit, for example by the CPU of the endoscope reprocessing device. In this case, the data or the program and the routine, respectively, can be provided as a data stream. It can be temporarily stored in the processor of the flow control unit during execution of the reprocessing routine.

The processing fluid can be a reprocessing fluid, for example a fluid for cleaning and/or a fluid for disinfection. Furthermore, the processing fluid can be compressed air. Compressed air can be applied to blow out reprocessing fluid from the internal channels of the endoscope. Furthermore, the compressed air can be used for drying of the channels of the endoscope.

The processing fluid can be compressed air only, which means that no reprocessing fluid is applied. In this scenario, the technical effect caused by the flow control unit can be advantageous. This is because the dedicated switchable valves are set to the safe state at the end of the reprocessing routine. If the processing fluid is compressed air, this measure reduces the compressed air consumption of the reprocessing device.

In every use case, which means in a situation in which the processing fluid is compressed air or the processing fluid is a reprocessing fluid or the processing fluid is a mixture of the reprocessing fluid and compressed air, the flow rate through the main supply line is lower than a maximum flow rate. This reduces the consumption of processing fluid at the end of the reprocessing routine.

The reason why this measure can be advantageous can be understood when considering that in a default state of the flow control unit all switchable valves are fully open. In a conventional flow control units, the switchable valves are set to this fully open position at the end of the reprocessing routine. However, in this switching state, the consumption of processing fluid is very high, if processing fluid is supplied to the flow control unit. This can be avoided. By setting the dedicated switchable valves to the save state, the processing fluid consumption of the flow control unit can be significantly reduced. This can be very advantageous if the processing fluid is compressed air. The endoscope reprocessing device including the flow control unit will not negatively impact a centralized air supply system to which the endoscope reprocessing device is connected. As outlined before, such effect can eventually occur. This can be advantageously avoided.

The flow control unit can be further configured in that the processor can be further configured to set the dedicated switchable valve to a switching position lastly defined in the reprocessing routine, as the safe switching state. The lastly defined switching position of the dedicated switchable valve will in many cases not be the fully open position. By setting the switchable valve to such position, which is lastly defined in the reprocessing routine, the total consumption of processing fluid of the flow control unit can be significantly reduced.

Furthermore, the flow control unit can be configured in that the processor can be further configured to set the dedicated switchable valve to a predetermined safe switching position, wherein in the predetermined safe switching position, a flow rate through the dedicated switchable valve can be lower than a maximum possible flow rate through the dedicated switchable valve, for example, the safe switching position is the closed position of the dedicated switchable valve.

The safe switching position can be for example a position in which a flow through the switchable valve is 80%, 50% or 20% of the maximum flow. This will significantly reduce the flow rate through the flow control unit.

The flow rate through the switchable valve can be a function of the opening position of the switchable valve. In other words, instead of referring to the flow rate, reference can be made to an opening position. For example, the safe switching position can be defined by an opening position which is 80%, 50% or 20% of the fully open position. Generally speaking, the same or very similar technical effect can be achieved when making reference to the opening position instead of the flow.

The flow control unit can comprise a plurality of supply channels. A dedicated switchable valve can be included in every supply channel. The processor of the flow control unit can be configured to set the switchable valves of this plurality of supply channels to positions in that a total flow rate through the flow control unit is lower than a maximum total flow rate through the flow control unit. The total flow is the flow in the main supply line because all supply channels branch off the main supply line. In the flow control unit, which can comprise a plurality of supply channels, the individual switching positions of the switchable valves can be different. It is furthermore not necessary to refer to the individual switching position, because the total flow through the flow control unit can be influenced by the switching position of all switchable valves. For example, in a flow control unit comprising four dedicated switchable valves, a first valve can be fully open while the second, third and fourth valve can be fully closed. The total flow through the control unit, which is the flow in the main supply line, will be reduced by three quarters when compared to a situation in which all valves are fully open (default position). In other words, when the flow control unit is configured to comprise a plurality of supply channels, the switching positions of the switchable valves can be set in that the total flow through the flow control unit is reduced. This can include suitable setup of setting positions of one or more of the plurality of valves.

Furthermore, the flow control unit can be configured in that it can further comprise a sensor, which can be configured to detect the presence of processing fluid at the inlet, wherein the processor can be further configured to terminate the safe switching state of the at least one switchable valve and to set the switchable valve to a default switching state, if a measurement value of the sensor is indicative of the absence of processing fluid at the inlet.

The sensor can be for example a pressure sensor. For example, the sensor can be integrated in the main supply line. If there is no pressure in the main supply line, it can be assumed that no processing fluid is provided at the inlet of the flow control unit. If there is no more processing fluid supplied to the flow control unit, the switchable valves can be set to the default switching state, which can be for example the fully open position.

Furthermore, the flow control unit can comprise a timer, which can be configured to start when the reprocessing routine is terminated, wherein the processor can be further configured to terminate the safe switching state of the at least one switchable valve and to set the switchable valve to a default switching state, if the timer indicates that a predetermined period of time expired.

The timer can be implemented in the processor of the flow control unit. The period of time, which can be counted by the timer, can be set to a value, after expiration of which, it can be assumed that no more processing fluid is provided to the flow control unit under normal operating conditions of the reprocessing device. Consequently, it can be assumed that it is safe to set the switchable valves to the default switching state after expiration of the period of time.

Furthermore, the flow control unit can be configured in that the processor can be further configured to terminate the safe switching state of the at least one switchable valve and to set the switchable valve to a default switching state, if the processor receives a termination signal, instructing the processor to set the switchable valve to a default switching state.

The termination signal can be generated by a central processor of the endoscope reprocessing device. This central processor can hold information on the basis of which the central processor can decide whether or not there is processing fluid provided or fed to the flow control unit. This can apply if the processing fluid is compressed air.

The default switching state can be a switching state in which the switchable valve is fully open. This can apply to the at least one dedicated switchable valve in a same way as for a plurality of dedicated switchable valves.

When the flow control unit is set to its default state, the endoscope reprocessing device can find the flow control unit in a state, which is well-established and known to many routines. For example, no changes at the endoscope reprocessing device are necessary for handling of general standby of the endoscope reprocessing device. On the other hand, excessive processing fluid consumption, for example excessive consumption of compressed air, can be avoided during operation of the flow control unit.

Such object can be further solved by an endoscope reprocessing device comprising the flow control unit according to one or more of the aforementioned aspects. Furthermore, the endoscope reprocessing device can comprise the fluid source, which is a first source of a reprocessing fluid and a second source of pressurized air, wherein the first and the second source can be coupled to a 3/2-valve and an outlet of the 3/2-valve can be coupled to the inlet of the flow control unit.

Same or similar advantageous, which have been mentioned with respect to the flow control unit apply to the endoscope reprocessing device in the same or similar way and shall be therefore not repeated.

Such object can also be solved by a method of operating a flow control unit for an endoscope reprocessing device, the flow control unit comprising:
  a main fluid supply line, coupled to an inlet,
  at least one supply channel fluidically coupled to the main fluid supply line,
  at least one dedicated switchable valve intergrated in the supply channel, and
  a processor comprising hardware,
  the method comprising:
  providing a processing fluid from a fluid source to the flow control unit via the inlet,
  supplying the processing fluid from the inlet to the main fluid supply line and further to at least one supply channel,
  operating the processor in that the at least one dedicated switchable valve is opened and closed to allow the processing fluid to flow through the supply channel and further to an internal channel of the endoscope or to block the processing fluid in the supply channel, wherein the processor opens and closes the dedicated switchable valve according to a reprocessing routine,
  further operating the processor, in that upon termination of the reprocessing routine, the processor sets the at least one switchable valve to a safe switching state, wherein in the safe switching state a flow rate through the main supply line is lower than a maximum flow rate through the main supply line.

Also to the method of operating the flow control unit, same or similar advantageous and aspects which have been mentioned with respect to the flow control unit apply in the same or similar way. They shall not be repeated.

The method can set the dedicated switchable valve to a switching position lastly defined in the reprocessing routine, as the safe switching state.

Furthermore, the method can set the dedicated switchable valve to a predetermined safe switching position, wherein in the predetermined safe switching position, a flow rate through the dedicated switchable valve can be lower than a maximum flow rate through the dedicated switchable valve, for example, the safe switching position is the closed position of the dedicated switchable valve.

In the method, the flow control unit can further comprise a sensor configured to detect the presence of processing fluid at the inlet, wherein the processor can be further operated to terminate the safe switching state of the at least one switchable valve and to set the switchable valve to a default switching state, if the sensor measures a measurement value, which is indicative of the absence of processing fluid at the inlet.

In the method, the flow control unit can further comprise a timer and the processor can start the timer when the reprocessing routine is terminated, wherein the processor can terminate the safe switching state of the at least one switchable valve and set the switchable valve to a default switching state, if the timer indicates that a predetermined period of time expired.

Finally, in the method, the processor can terminate the safe switching state of the at least one switchable valve and set the switchable valve to a default switching state, if the processor receives a termination signal, instructing the processor to set the switchable valve to a default switching state.

Furthermore, such object can be solved by a method of operating an endoscope reprocessing device according to aspects of the present disclosure, wherein the method comprising:
  providing a flow of processing fluid from the first fluid source or the second fluid source to the 3/2-valve and further to the inlet of the flow control unit,
  supplying the processing fluid from the inlet to the main fluid supply line and further to at least one supply channel,
  operating the processor in that the at least one dedicated switchable valve is opened and closed to allow the processing fluid to flow through the supply channel and further to an internal channel of the endoscope or to block the processing fluid in the supply channel, wherein the processor opens and closes the dedicated switchable valve according to a reprocessing routine,
  further operating the processor, in that upon termination of the reprocessing routine, the processor sets the at least one switchable valve to a safe switching state, wherein in the safe switching state a flow rate through the main supply line is lower than a maximum flow rate through the main supply line.

With respect to the method of operating the endoscope reprocessing device same or similar advantageous and aspects which have been mentioned with respect to the flow control unit apply in the same or similar way.

In the method, upon termination of the reprocessing routine, the processor can operate the 3/2-valve in that compressed air is supplied as the processing fluid, and wherein the processor can be further operated in that the dedicated switchable valve can be set to a predetermined safe switching position, in which a flow rate through the dedicated switchable valve can be lower than a maximum possible flow rate through the dedicated switchable valve, for example, the processor can be further operated in that the dedicated switchable valve can be set to a closed position.

BRIEF DESCRIPTION OF THE DRAWINGS

Further features will become evident from the description of embodiments, together with the claims and the appended drawings. Embodiments can fulfill individual features or a combination of several features.

The embodiments described below, without restricting the general intent of the invention, based on exemplary embodiments, wherein reference is made expressly to the drawings with regard to the disclosure of all details that are not explained in greater detail in the text.

In the drawings:

FIG. 1 illustrates a schematic endoscope reprocessing device,

FIG. 2 illustrates a flow chart of a method of operating the flow control unit, and FIG. 3 illustrates a flow chart of a method of operating the endoscope reprocessing device.

In the drawings, the same or similar types of elements or respectively corresponding parts are provided with the same reference numbers in order to prevent the item from needing to be reintroduced.

DETAILED DESCRIPTION

Figure 1:
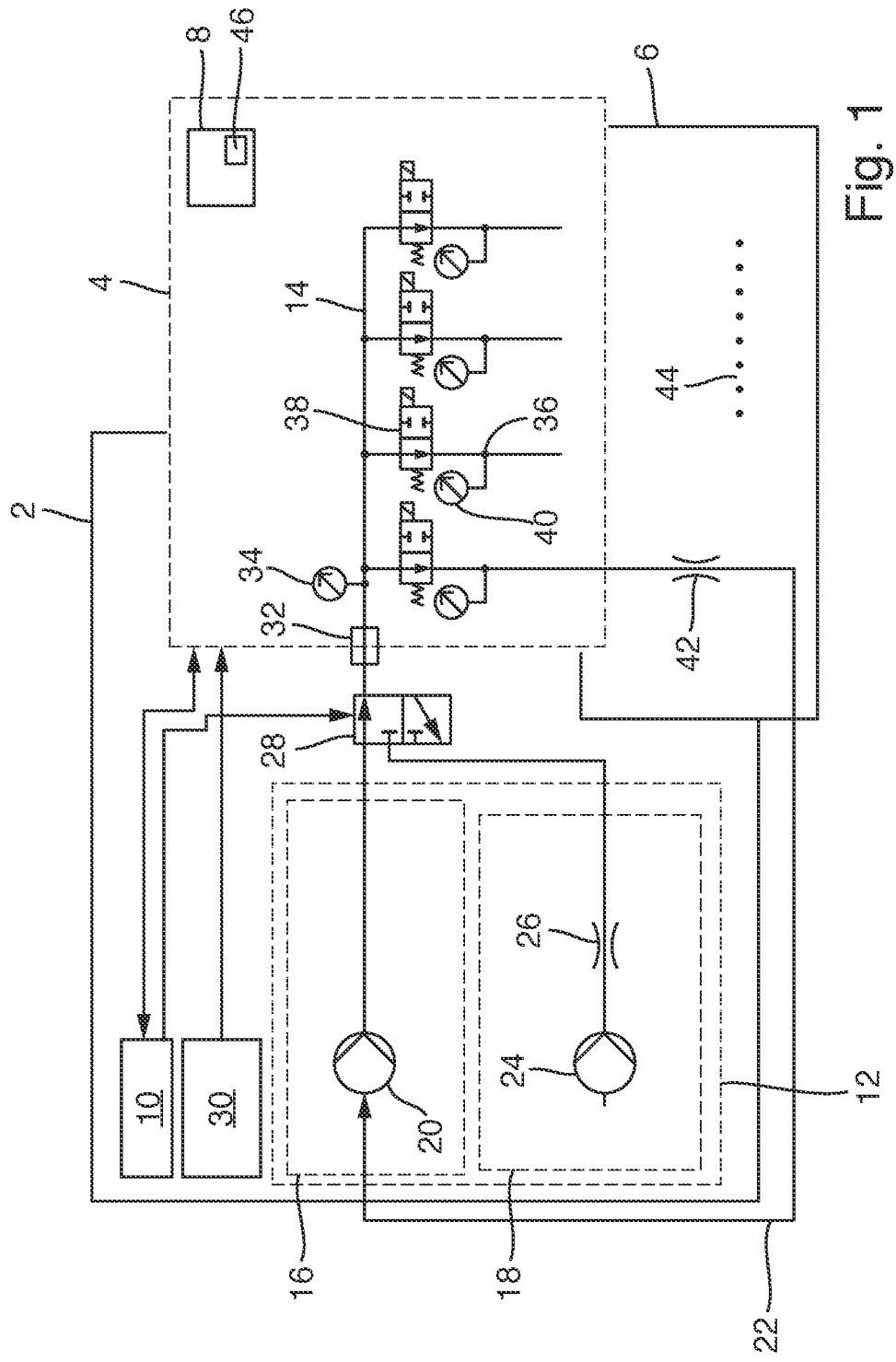

FIG. 1 shows a schematic illustration of an endoscope reprocessing device 2. The endoscope reprocessing device 2 includes a flow control unit 4 and a washing cabinet 6. The flow control unit 4 can be an integral part of the endoscope reprocessing device 2. The flow control unit 4 comprises a processor 8, which is configured to operate the flow control unit 4. The processor comprising hardware, such as a CPU, which can access software for carrying out its intended functions. The endoscope reprocessing device 2 comprises a central processor 10 for operating the endoscope reprocessing device 2. The central processor comprising hardware, such as a CPU, which can access software for carrying out its intended functions. The processor 8 of the flow control unit 4 can also be implemented in the central processor 10 of the endoscope reprocessing device 2. The communication between the central processor 10 and the flow control unit 4 is provided by a data link, which can be a wired or a wireless data link and is indicated by a double arrow.

The endoscope reprocessing device 2 includes a processing fluid source 12, which provides processing fluid to a main fluid supply line 14. The processing fluid source 12 comprises a reprocessing fluid source 16 and a pressurized air source 18, which supply a reprocessing fluid and pressurized air, respectively, to endoscopes (not shown) that have been put into washing baskets inside the washing cabinet 6 and are connected to adapters that are ultimately connected to the reprocessing fluid source 16 and the pressurized air source 18, respectively. The reprocessing fluid source 16 comprises a pump 20, for example a circulation pump, receiving the reprocessing fluid (which can be a reprocessing liquid) back from the washing cabinet 6, by way of a conduit 22. The pump 20 can circulate the reprocessing fluid through other parts, such as a filter or a secondary pump tasked with providing the required flow rate and pressure of the reprocessing fluid to the endoscopes to be reprocessed. The pressurized air source 18 can have a compressor or air pump as an air source 24, which supplies pressurized air for various purposes to the endoscopes. However, the air source 24 can also be an inlet, which is connected to a centralized air supply system of for example a medical facility, in which the endoscope reprocessing device 2 is operated. The flow rate and pressure of the pressurized air flow to the main fluid supply line 14 and later to the endoscopes can be controlled or regulated by an adjustment valve 26.

Between the processing fluid supply 12 and the flow control unit 4, there is a 3/2 switching valve 28, which can be electronically controlled and actuated pneumatically, hydraulically or electrically. The 3/2 switching valve 28 is configured to switch back and forth between supply of reprocessing fluid from reprocessing fluid source 16 and pressurized air from pressurized air source 18 to the main fluid supply line 14. Control of the switching valve 28 is performed by the central processor 10. This is indicated by an arrow. Another component of the endoscope reprocessing device 2 is a power supply 30, which is configured to provide the endoscope reprocessing device 2 and the flow control unit 4 with electrical power.

The flow control unit 4 comprises the main fluid supply line 14, which is coupled to an inlet 32 at which the flow control unit 4 receives the processing fluid, i.e. the reprocessing fluid or compressed air, from the respective source 16, 18. Depending on the switching status of the 3/2 switching valve 28, the flow control unit 4 either receives reprocessing fluid or compressed air. In the main fluid supply line 14, there is a sensor 34, for example a pressure sensor, which is configured to detect the presence of processing fluid at the inlet 32. The sensor data is analyzed by the processor 8 of the flow control unit 4.

The main fluid supply line 14 branches off into a plurality of supply channels 36. A respective one of the supply channels 36 leads to an adapter or to adapters at the interface to the washing cabinet 6 to which the channels of the endoscopes to be reprocessed will be connected. By way of an example only, FIG. 1 shows an endoscope reprocessing device 2 having four supply channels 36, only one of which is provided with a reference number for the sake of clarity. The other supply channels 36 are outfitted in similar fashion and may vary in diameter or other parameters depending on the type of endoscope channels to which they are usually connected. In place of the four supply channels 36 depicted here, fewer or more supply channels 36 can be foreseen, as the case may be.

A respective one of the supply channels 36 is fluidly coupled to the main fluid supply line 14 and a respective one of the supply channels 36 comprises a dedicated switchable valve 38 that is integrated in the supply channel 36. The dedicated switchable valves 38 can be electronically controlled and operated pneumatically, hydraulically or electrically. The dedicated switchable valves 38 are controlled by the processor 8 of the flow control unit 4. Furthermore, there can be a dedicated sensor 40 integrated in a respective one of the supply channels 36. The dedicated sensor 40 is for sensing of a pressure in the assigned supply channel 36. Sensor data is analyzed by the processor 8, which, based on this information, can for example detect the switching position of the dedicated switchable valve 38.

The processor 8 of the flow control unit 4 can have a dedicated main board logically controlling operations of components of the flow control unit 4. This dedicated main board can be in data communication with the central processor 10 and receive commands to be carried out by the flow control unit 4. This dedicated main board can, however, also be implemented as software in the central processor 10.

For each of the supply channels 36 of the flow control unit 4, the washing cabinet 6 has a coupling to an internal endoscope channel 42. This is illustrated as a constriction to the flow of processing fluid in FIG. 1. The depicted constriction shall represent for example an adapter and the internal endoscope channel to the supply channel 36. Furthermore, identical couplings 44 corresponding to the other supply channels 36 are schematically illustrated using a series of dots.

The dedicated switchable valve 38 is configured to open or close the supply channel 36 in that the flow of the processing fluid passes through the supply channel 36 or is blocked. The processor 8 is configured to operate the dedicated switchable valves 38 according to a reprocessing routine. The reprocessing routine is a part of a reprocessing program, which the endoscopes undergoes after use. A reprocessing program can comprise one or more reprocessing routines that can be repeatedly applied and furthermore can be applied for different purposes. For example, a reprocessing routine can comprise the reprocessing routines: "washing and disinfection" and "drying". During execution of the reprocessing routine, the processor 8 performs various switching operations of the dedicated switchable valves 38. Due to this switching operations, the various internal channels of the endoscopes are provided with either reprocessing fluid or compressed air in a predetermined sequence, according to the reprocessing program and reprocessing routine, respectively.

The processor 8 is further configured to set the dedicated switchable valves 38 to a safe switching state upon termination of the reprocessing routine. In the safe switching state, a flow rate through the main supply line 14 is lower than a maximum flow rate through the main supply line 14. In other words, setting the dedicated switchable valves 38 to the safe switching state significantly reduces the flow through the main supply line 14. This applies for example when the main supply line 14 is connected to the pressurized air source 18. Furthermore, the air source 24 is an inlet to a coupling to a centralized air supply of for example a medical facility. The setting of the dedicated switchable valves 38 to the safe switching state results in significantly lower air flow from a centralized air supply through the main fluid supply line 14 and hence reduces the compressed air consumption of the endoscope reprocessing device 2. This can enhance the stability of the centralized air supply system.

The flow control unit 4 can be for example configured in that the processor 8 is further configured to set the dedicated switchable valves 38 to a switching position lastly defined in the reprocessing routine as the safe switching state. The switching state lastly defined in the reprocessing routine will very rarely be a position in which all dedicated switchable valves 38 are fully open. Hence, by setting the dedicated switchable valves 38 to the switching state lastly defined in the reprocessing routine will significantly reduce the flow through the main supply line 14.

Furthermore, the flow control unit 4 can be configured in that the processor 8 is further configured in that the dedicated switchable valves 38 are set to a predetermined safe switching position. This predetermined safe switching position can be for example the closed position. It can also be a position in which the dedicated switchable valves 38 are partly open, for example 10%, 30% or even 50%. In the predetermined safe switching position, a flow rate through the dedicated switchable valve 38 is lower than a maximum possible flow rate through the dedicated switchable valve 38. The processor can also set the various dedicated switchable valves 38 to positions in which some of the dedicated switchable valves 38 are fully open and other dedicated switchable valves 38 are fully closed. If for example three of the four depicted dedicated switchable valves 38 are fully closed and one of the dedicated switchable valves 38 remains fully open, the flow through the main supply line 14 will be reduced by three quarters in comparison to a maximum flow rate.

The flow control unit 4 can be further configured in that the data of the sensor 34 in the main supply line 14 is used to detect the presence of processing fluid at the inlet 32. If for example the pressure at the sensor 34 is zero or near to zero, it is reasonable to assume that no processing fluid is provided at the inlet 32. In this case, the processor 8 can terminate the safe switching state of the dedicated switchable valves 38 and set the dedicated switchable valves 38 to a default switching state. The default switching state of the dedicated switchable valves 38 can be the fully open state.

The flow control unit 4 can be further configured to have a timer 46. Such timer 46 can be provided in the processor 8. The timer 46 is configured to start when the reprocessing routine is terminated. The processor 8 will terminate the safe switching state of the dedicated switchable valves 38 and to set these valves 38 to the default switching state, if the timer 46 indicates that the predetermined period of time expired.

The processor 8 of the flow control unit 4 can be configured to terminate the safe switching state of the dedicated switchable valves 38 and to set these valves 38 to the default switching state, if the processor 8 receives a termination signal from the central processor 10. This termination signal instructs the processor 8 to set the dedicated switchable valves 38 to the default switching state.

Figure 2:
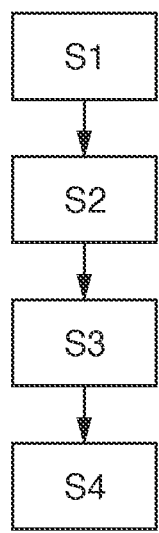

FIG. 2 illustrates a flow chart showing a method of operating a flow control unit 4. The flow control unit 4 has been explained with reference to FIG. 1. The method comprises the following steps: in step S1, a processing fluid is provided from one of the fluid sources 16, 18 to the flow control unit 4 via the inlet 32. In step S2, the processing fluid is supplied from the inlet 32 to the main fluid supply line 14 and further to at least one of the supply channels 36. In step S3, the processor 8 is operated in that at least one of the dedicated switchable valves 36 is opened to allow the processing fluid, which means reprocessing fluid or compressed air, to flow through the dedicated supply channels 36 and further to an internal channel of the endoscope, or to block the processing fluid in the dedicated supply channel 36. In step S3, the processor 8 opens and closes the dedicated switchable valves 36 according to a reprocessing routine. In step S4, the processor 8 is further operated in that upon termination of the reprocessing routine the switchable valves 38 are set to the safe switching state, wherein in the safe switching state, the flow rate through the main supply line 14 is lower than a maximum flow rate through the main supply line 14.

Figure 3:
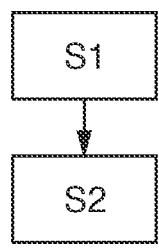

In FIG. 3 there is a flow chart illustrating a method of operating the endoscope reprocessing device 2. The method comprises the following steps: in step S1, a flow of processing fluid from the reprocessing fluid source 16 or the pressurized air source 18 is provided to the switchable valve 28, which can be a 3/2-valve. The flow is further provided to the inlet 32 of the flow control unit 4. In step S2, the flow control unit 4 is operated as outlined with reference to FIG. 2.

The central processor 10 can be operated in that the switchable valve 28 receives compressed air as the processing fluid and the processor 8 of the flow control unit 4 is operated in that the dedicated switchable valves 38 are set to the predetermined safe switching position in which the flow rate through the main supply line 14 is reduced. Performance of these method steps reduces the consumption of compressed air of the endoscope reprocessing device 2.

While there has been shown and described what is considered to be embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

LIST OF REFERENCE SIGNS

- 2 endoscope reprocessing device
- 4 flow control unit
- 6 washing cabinet
- 8 processor
- 10 central processor
- 12 processing fluid source
- 14 main fluid supply line
- 16 reprocessing fluid source
- 18 pressurized air source
- 20 pump
- 22 duct
- 24 air source
- 26 adjustment valve
- 28 3/2 switching valve
- 30 power supply
- 32 inlet
- 34 sensor
- 36 supply channel
- 38 dedicated switchable valve
- 40 dedicated sensor
- 42 internal endoscope channel
- 44 couplings
- 46 timer

What is claimed is:

1. A flow control unit for use with an endoscope reprocessing device, the flow control unit comprising:
   - a main fluid supply line coupled to an inlet, wherein the inlet is configured to receive processing fluid from a fluid source,
   - at least one supply channel for supplying the processing fluid to at least one internal channel of an endoscope, wherein the at least one supply channel is fluidically coupled to the main fluid supply line,
   - at least one dedicated switchable valve integrated in the supply channel, wherein the switchable valve is configured to open the supply channel to pass a flow of the processing fluid through the supply channel or close the supply channel to block the flow of the processing fluid, and
   - a processor comprising hardware, the processor being configured to:
     - operate the at least one dedicated switchable valve according to a reprocessing routine, and
     - upon termination of the reprocessing routine, set the at least one dedicated switchable valve to a safe switching state, wherein in the safe switching state a flow rate through the main supply line is lower than a maximum flow rate through the main supply line.

2. The flow control unit according to claim 1, wherein the processor is further configured to set the dedicated switchable valve to a switching position lastly defined in the reprocessing routine, as the safe switching state.

3. The flow control unit according to claim 1, wherein the processor is further configured to set the dedicated switchable valve to a predetermined safe switching position, wherein in the predetermined safe switching position, a flow rate through the dedicated switchable valve is lower than a maximum possible flow rate through the dedicated switchable valve.

4. The flow control unit according to claim 3, wherein the safe switching position is the closed position of the dedicated switchable valve.

5. The flow control unit according to claim 1, further comprising a sensor configured to detect the presence of processing fluid at the inlet, wherein the processor is further configured to terminate the safe switching state of the at least one switchable valve and set the switchable valve to a default switching state, if a measurement value of the sensor is indicative of the absence of processing fluid at the inlet.

6. The flow control unit according to claim 1, further comprising a timer configured to start when the reprocessing routine is terminated, wherein the processor is further configured to terminate the safe switching state of the at least one switchable valve and set the switchable valve to a default switching state, if the timer indicates that a predetermined period of time has expired.

7. The flow control unit according to claim 1, wherein the processor is further configured to terminate the safe switching state of the at least one switchable valve and set the switchable valve to a default switching state, if the processor receives a termination signal, instructing the processor to set the switchable valve to a default switching state.

8. An endoscope reprocessing device comprising:
   - the flow control unit according to claim 1;
   - the fluid source, is the fluid source comprising a first source of a reprocessing fluid and a second source of pressurized air,
   - wherein the first source and the second source are coupled to a 3/2-valve and an outlet of the 3/2-valve is coupled to the inlet of the flow control unit.

9. A method of operating an endoscope reprocessing device having a flow control unit, the flow control unit comprising:
   - a main fluid supply line coupled to an inlet,
   - at least one supply channel fluidically coupled to the main fluid supply line, and
   - at least one dedicated switchable valve integrated in the supply channel,
   - the method comprising:
     - providing a processing fluid from a fluid source to the flow control unit via the inlet,
     - supplying the processing fluid from the inlet to the main fluid supply line and further to at least one supply channel,
     - opening and closing the at least one dedicated switchable valve to allow the processing fluid to flow through the supply channel and further to an internal channel of the endoscope or to block the processing fluid in the supply channel according to a reprocessing routine, and
     - upon termination of the reprocessing routine, set the at least one switchable valve to a safe switching state, wherein in the safe switching state a flow rate through the main supply line is lower than a maximum flow rate through the main supply line.

10. The method according to claim 9, wherein the dedicated switchable valve is set to a switching position lastly defined in the reprocessing routine, as the safe switching state.

11. The method according to claim 9, wherein the dedicated switchable valve is set to a predetermined safe switching position, wherein in the predetermined safe switching position, a flow rate through the dedicated switchable valve is lower than a maximum flow rate through the dedicated switchable valve.

12. The method according to claim 11, wherein the safe switching position is the closed position of the dedicated switchable valve.

13. The method according to claim 9, wherein the flow control unit further comprises a sensor configured to detect the presence of processing fluid at the inlet, wherein the method further comprises terminating the safe switching state of the at least one switchable valve and setting the switchable valve to a default switching state, if the sensor measures a measurement value, which is indicative of the absence of processing fluid at the inlet.

14. The method according to claim 9, wherein the flow control unit further comprises a timer and the method further comprises:
   starting the timer when the reprocessing routine is terminated, and
   terminating the safe switching state of the at least one switchable valve and setting the switchable valve to a default switching state if the timer indicates that a predetermined period of time has expired.

15. The method according to claim 9, wherein the method further comprises terminating the safe switching state of the at least one switchable valve and setting the switchable valve to a default switching state upon receiving instructions to set the switchable valve to a default switching state.

16. A method, according to claim 9, wherein the endoscope reprocessing device comprising:
   a fluid source comprising a first source of a reprocessing fluid and a second source of pressurized air, and
   wherein the first source and the second source are coupled to a 3/2-valve and an outlet of the 3/2-valve is coupled to the inlet of the flow control unit
the method further comprising:
   providing a flow of processing fluid from the first source or the second fluid source to the 3/2-valve and further to the inlet of the flow control unit, and
   supplying the processing fluid from the inlet to the main fluid supply line and further to at least one supply channel.

17. The method according to claim 16, wherein, upon termination of the reprocessing routine, the 3/2-valve is operated to supply compressed air as the processing fluid and the dedicated switchable valve is set to a predetermined safe switching position, in which a flow rate through the dedicated switchable valve is lower than a maximum possible flow rate through the dedicated switchable valve.

18. The method according to claim 17, wherein the dedicated switchable valve is set to a closed position.

19. A control apparatus of operating a flow control unit for an endoscope reprocessing device, the control apparatus comprising:
   a processor comprising hardware, the processor being configured to:
      provide a processing fluid from a fluid source to the flow control unit via a main fluid supply line coupled to an inlet,
      supply the processing fluid from the inlet to the main fluid supply line and further to at least one supply channel fluidically coupled to the main fluid supply line,
      open and close at least one dedicated switchable valve integrated in the supply channel to allow the processing fluid to flow through the supply channel and further to an internal channel of the endoscope or to block the processing fluid in the supply channel according to a reprocessing routine, and
      upon termination of the reprocessing routine, set the at least one switchable valve to a safe switching state, wherein in the safe switching state a flow rate through the main supply line is lower than a maximum flow rate through the main supply line.

* * * * *